United States Patent
Pauws et al.

(10) Patent No.: US 11,510,572 B2
(45) Date of Patent: Nov. 29, 2022

(54) METHOD AND APPARATUS FOR DETECTING CLINICAL DETERIORATION IN PATIENTS ON A TELEHEALTH SERVICE

(71) Applicant: KONINKLIJKE PHILIPS N.V., Eindhoven (NL)

(72) Inventors: Steffen Clarence Pauws, Eindhoven (NL); Daniele De Massari, Eindhoven (NL); Nicolaas Gregorius Petrus Den Teuling, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 186 days.

(21) Appl. No.: 16/084,255

(22) PCT Filed: Mar. 16, 2017

(86) PCT No.: PCT/IB2017/051523
§ 371 (c)(1),
(2) Date: Sep. 12, 2018

(87) PCT Pub. No.: WO2017/158545
PCT Pub. Date: Sep. 21, 2017

(65) Prior Publication Data
US 2019/0069779 A1    Mar. 7, 2019

Related U.S. Application Data

(60) Provisional application No. 62/309,634, filed on Mar. 17, 2016.

(51) Int. Cl.
*A61B 5/00* (2006.01)
*G16H 50/30* (2018.01)
(Continued)

(52) U.S. Cl.
CPC .......... *A61B 5/0022* (2013.01); *A61B 5/7275* (2013.01); *G16H 40/63* (2018.01);
(Continued)

(58) Field of Classification Search
CPC ........ G16H 50/50; G16H 50/30; G16H 50/20; A61B 5/0022; A61B 5/7275
(Continued)

(56) References Cited

U.S. PATENT DOCUMENTS

2006/0129427 A1* 6/2006 Wennberg ............... G06Q 40/08
                                                        705/2
2011/0009760 A1  1/2011 Zhang et al.
(Continued)

FOREIGN PATENT DOCUMENTS

WO    WO-2015128842 A1 *  9/2015 ........... A61B 5/0816

OTHER PUBLICATIONS

Akshay S. Desai, Rehospitalization for Heart Failure Predict or Prevent? Jul. 24, 2012 https://doi.org/10.1161/CIRCULATIONAHA.112.125435 Circulation. 2012;126:501-506 (Year: 2012).*
(Continued)

*Primary Examiner* — Hiep V Nguyen

(57) ABSTRACT

A system for detecting clinical deterioration in a patient having a health condition during one or more post-discharge patient follow-up periods is provided. The system includes a computer system that has one or more physical processors programmed with computer program instructions which, when executed cause the computer system to: determine a clinical deterioration risk detection model for each of the post-discharge patient follow-up periods, and determine a clinical deterioration risk detection value for the patient in the post-discharge patient follow-up period using the corresponding clinical deterioration risk detection model. The clinical deterioration risk detection model is a function of
(Continued)

health information of the patient in the corresponding post-discharge patient follow-up period. The clinical deterioration risk detection value is configured to predict the likelihood of the clinical deterioration in the patient in the post-discharge patient follow-up period.

15 Claims, 4 Drawing Sheets

(51) Int. Cl.
    *G16H 50/70*     (2018.01)
    *G16H 50/50*     (2018.01)
    *G16H 40/63*     (2018.01)
    *G16H 40/67*     (2018.01)

(52) U.S. Cl.
    CPC ............. *G16H 40/67* (2018.01); *G16H 50/30* (2018.01); *G16H 50/50* (2018.01); *G16H 50/70* (2018.01)

(58) Field of Classification Search
    USPC .............................................................. 705/2
    See application file for complete search history.

(56) References Cited

U.S. PATENT DOCUMENTS

| | | | | |
|---|---|---|---|---|
| 2011/0313788 A1* | 12/2011 | Amland | ................. | G16H 50/30 705/3 |
| 2013/0290005 A1* | 10/2013 | Vesto | .................... | G06Q 10/06 705/2 |
| 2014/0136227 A1* | 5/2014 | Amland | .................. | G06F 19/00 705/2 |
| 2014/0207492 A1 | 7/2014 | Farooq et al. | | |
| 2014/0350967 A1 | 11/2014 | Geleijnse et al. | | |
| 2015/0213202 A1* | 7/2015 | Amarasingham | ....... | G06F 19/00 705/2 |

OTHER PUBLICATIONS

Rehospitalization for Heart Failure: Problems and Perspectives; Journal of the American College of Cardiology 61.4: 391-403. Elsevier Limited. (Jan. 29, 2013) (Year: 2013).*

Ledwidge, M. et al., "Can individualized weight monitoring using the HeartPhone algorithm improve sensitivity for clinical deterioration of heart failure?", European Journal of Heart Failure (2013) 15, 447-455.

Lewin, J. et al., "Clinical deterioration in established heart failure: What is the value of BNP and weight gain in aiding diagnosis?", The European Journal of Heart Failure 7 (2005) 953-957.

Chun, S., Tu, J. V., Wijeysundera, H. C., Austin, P. C., Wang, X., Levy, D., & Lee, D. S. (2012). Lifetime analysis of hospitalizations and survival of patients newly admitted with heart failure. Circulation: Heart Failure, 5(4), 414-421. doi:10.1161/CIRCHEARTFAILURE.111.964791.

Desai, A. S., & Stevenson, L. W. (2012) Rehospitalization for heart failure: Predict or prevent? Circulation, 126(4), 501-506. doi: 10.1161/CIRCULATIONAHA.112.125435.

* cited by examiner

METHOD AND APPARATUS FOR DETECTING CLINICAL DETERIORATION IN PATIENTS ON A TELEHEALTH SERVICE

CROSS-REFERENCE TO PRIOR APPLICATIONS

This application is the U.S. National Phase application under 35 U.S.C. § 371 of International Application No. PCT/IB2017/051523, filed on 16 Mar. 2017, which claims the benefit of U.S. Provisional Patent Application No. 62/309,634, filed on 17 Mar. 2016. These applications are hereby incorporated by reference herein.

BACKGROUND

1. Field

The present disclosure pertains to a method and an apparatus for detecting clinical deterioration in patients on a telehealth service, and, in particular, for detecting clinical deterioration in patients with a chronic health condition during one or more post-discharge patient follow-up periods.

2. Description of the Related Art

Chronically ill patients are managed by a telehealth service to prevent them from going back to the hospital for an emergency admission and to improve their quality of life. One of the leading reasons for an unplanned admission to the hospital is an abrupt worsening of the patient condition.

The telehealth service provides remote patient monitoring and aims at detecting patient's worsening conditions in time by means of predictive algorithms. For example, these predictive algorithms use daily patient vital sign data or readings (e.g., blood pressure (BP), heart rate (HR), body weight (BW) and oxygen saturation (SpO2)) and patient-reported signs and symptoms via surveys (e.g., edema, fatigue, shortness of breath (SoB), swelling of ankle, activity) to estimate patient's worsening conditions a few days before hospitalization. If a flag is raised in time, a timely intervention is possible by means of a patient-nurse encounter or a medication change.

However, nature and rate of exacerbations and acute episodes differ dramatically for chronic heart failure patients at various patient follow-up periods after discharge from the hospital where they were treated for their acute heart condition (e.g., heart failure), in particular, when considering a few days post-discharge, a month after discharge, many months after discharge and at the end-of-life. That is, nature and rate of exacerbations (hence, readmissions) vary over these post-discharge follow-up time periods of patients on telehealth, resulting in insufficient predictive performance of a clinical deterioration algorithm.

For example, when planning for the telehealth service for a patient after discharge from the hospital after their emergency, a cardiologist needs to estimate the prognosis of the patient by assessing symptoms and disease severity. The cardiology needs to decide whether (or not) 1) the patient has received his 'dry weight' by its diuresis therapy in the hospital, 2) venous pressure levels are at normal range, 3) the patient is at optimal medication, and 4) the patient responses are symptom-free.

This symptom assessment is difficult, as the patient may wrongly perceive that symptoms have been improved after a severe decompensation episode or because the patient has not returned yet to his everyday routines at home, outside the hospital. In addition, there may be also a greater willingness of a cardiologist to discharge the patient a few days earlier as the telehealth service will continue the titration or diuresis therapy and the patient monitoring at home. This can result in the patient being discharged too early when the patient condition has not yet sufficiently stabilized, risking an immediate re-admission when the patient arrives at home. Readmissions immediate after discharge (or, within the first week) are often an indication of incomplete treatment in the hospital, poor coordination of follow-ups or poor communication between patient and clinical staff on sodium and fluid intake and lifestyle changes at discharge. Exacerbations are expected to happen abruptly and frequently.

Early readmissions within the first to three months post-discharge can also be an indication of incomplete in-hospital treatment, poor follow-up coordination and insufficient patient routine of care plan or lifestyle recommendations. In addition, this follow-up time period overlaps with the 30 days in which hospitals are penalized for realizing higher than expected readmission rates. Also, exacerbations in this time window are expected to surface abruptly, but less than the phase immediately after discharge, and frequently.

After more than three months of telehealth use, routine should have been adopted, bad habits should have unlearned but patient boredom can creep in resulting in non-compliant behavior. In contrast to the early exacerbation, late exacerbations in heart failure are typically preceded by a gradual rise in ventricular filling pressures that begins in about two weeks in advance of detectable changes in weight or other overt clinical symptoms. Decompensation truly builds up over longer time interval before symptoms become apparent.

In an end-of-life scenario, heart failure severity has dramatically worsened in which marked symptoms of heart failure at rest are present. These patients experience frequent exacerbations which require frequent hospitalizations. Rather than just the telehealth service, the patient in this period need specialized interventions such as heart transplantation, implanted devices or palliative care.

Therefore, an improved system for managing chronically ill patients at various patient follow-up periods after discharge, in particular, when considering few days post-discharge, a month after discharge, many months after discharge and at the end-of-life is desired.

SUMMARY

Accordingly, it is an object of one or more embodiments of the present patent application to provide a system for detecting clinical deterioration in a patient having a health condition during one or more post-discharge patient follow-up periods. The system includes a computer system that has one or more physical processors programmed with computer program instructions which, when executed cause the computer system to: determine a clinical deterioration risk detection model for each of the post-discharge patient follow-up periods, the clinical deterioration risk detection model being a function of health information of the patient in the corresponding post-discharge patient follow-up period, and determine a clinical deterioration risk detection value for the patient in the post-discharge patient follow-up period using the corresponding clinical deterioration risk detection model, the clinical deterioration risk detection value being configured to predict the likelihood of the clinical deterioration in the patient in the post-discharge patient follow-up period.

It is yet another aspect of one or more embodiments of the present patent application to provide a method for detecting clinical deterioration in a patient having a health condition during one or more post-discharge patient follow-up periods. The method is implemented by a computer system that comprises one or more physical processors executing computer program instructions which, when executed, perform the method. The method includes determining, by the computer system, a clinical deterioration risk detection model for each of the post-discharge patient follow-up periods, the clinical deterioration risk detection model being a function of health information of the patient in the corresponding post-discharge patient follow-up period, and determining, by the computer system, a clinical deterioration risk detection value for the patient in the post-discharge patient follow-up period using the corresponding clinical deterioration risk detection model, the clinical deterioration risk detection value being configured to predict the likelihood of the clinical deterioration in the patient in the post-discharge patient follow-up period.

It is yet another aspect of one or more embodiments to provide a system for detecting clinical deterioration in a patient having a health condition during one or more post-discharge patient follow-up periods. The system includes a means for executing machine-readable instructions with at least one processor. The machine-readable instructions includes determining a clinical deterioration risk detection model for each of the post-discharge patient follow-up periods, the clinical deterioration risk detection model being a function of health information of the patient in the corresponding post-discharge patient follow-up period, and determining a clinical deterioration risk detection value for the patient in the post-discharge patient follow-up period using the corresponding clinical deterioration risk detection model, the clinical deterioration risk detection value being configured to predict the likelihood of the clinical deterioration in the patient in the post-discharge patient follow-up period.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
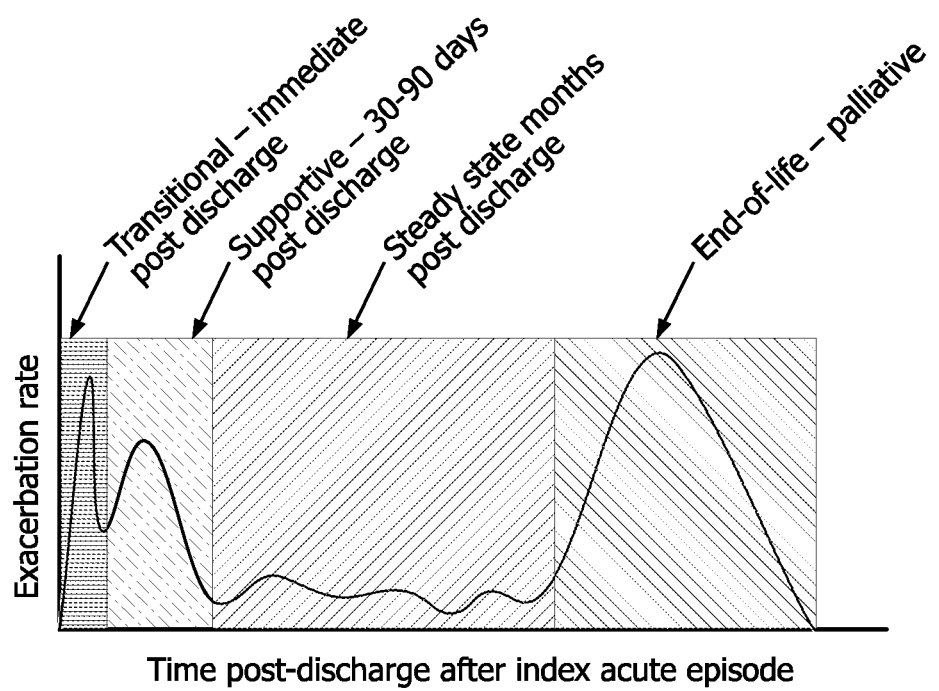
FIG. 1 is a graphical illustration of post-discharge patient follow-up periods in accordance an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 shows a graphical illustration of exacerbation rate measurements of patients having a chronic health condition (e.g., heart failure) in each of the phased patient follow-up periods after discharge (i.e., after being released from a hospital or other clinical setting where the patients were treated for their acute heart condition (e.g., heart failure) or other health condition). The graph in FIG. 1 illustrates patient follow-up time periods after an index actute episode (i.e., post-discharge) on its horizontal X-axis and exacerbation rate measurements on its vertical Y-axis.

Referring to FIG. 1, the present patent application provides time boundaries in post-discharge patient follow-up periods. For example, the post-discharge patient follow-up periods for a patient having a chronic heart condition may be classified into (a) transitional period or phase (TP), (b) supportive period or phase (SP), (c) steady state period or phase (SSP), and (d) end-of-life period or phase (EOLP).

In one embodiment, the transitional phase (TP) refers to a post-discharge patient follow-up period that is immediately after discharge (i.e., after being released from a hospital or other clinical setting where the patient was treated for his/her acute heart condition or other health condition). In one embodiment, the transitional phase (TP) is a post-discharge patient follow-up period that may be up to seven days after discharge (i.e., post-discharge). In one embodiment, the exacerbations in the transitional phase (TP) are expected to happen abruptly and frequently.

In one embodiment, the supportive phase (SP) refers to a post-discharge patient follow-up period that immediately follows the transitional phase (TP). In one embodiment, the supportive phase (SP) is a post-discharge patient follow-up period that may be 30 to 90 days after discharge (i.e., post-discharge). In one embodiment, the exacerbations in the supportive phase (SP) are expected to surface abruptly and frequently, but less than that in the transitional phase (TP).

In one embodiment, the steady state phase (SSP) refers to a post-discharge patient follow-up period that immediately follows the supportive phase (SP). In one embodiment, the steady state phase (SSP) is a post-discharge patient follow-up period that may be many months after discharge (post-discharge).

In one embodiment, the end-of-life phase (EOLP) refers to a post-discharge patient follow-up period that immediately follows the steady state phase (SSP). In one embodiment, in the end-of-life phase (EOLP), heart failure severity has dramatically worsened in which marked symptoms of heart failure at rest are present. The patients in the end-of-life phase (EOLP) may experience frequent exacerbations which require frequent hospitalizations. The patients in the end-of-life phase (EOLP) may also need specialized interventions such as heart transplantation, implanted devices or palliative care in addition to their telehealth service.

As can be seen from FIG. 1, nature and rate of exacerbations and, therefore, acute episodes differ dramatically for chronic heart failure patients at various patient follow-up periods after discharge from the hospital, in particular, when considering a few days post-discharge (or in the transitional phase (TP)), a month after discharge (or in supportive phase (SP)), many months after discharge (steady state phase (SSP)) and at the end-of-life (or in end-of-life phase (EOLP)). That is, nature and rate of exacerbations (hence, readmissions) vary over these post-discharge patient follow-up periods for patients on the telehealth service.

The present patent application provides a system 100 for detecting clinical deterioration in a patient having a health condition during one or more post-discharge patient follow-up periods (e.g., TP, SP, SSP, EOLP). As will be clear from the discussions below, system 100 includes a computer system 102 that has one or more physical processors programmed with computer program instructions which, when executed cause computer system 102 to determine a clinical deterioration risk detection model for each of the post-discharge patient follow-up periods, and determine a clinical deterioration risk detection value for the patient in the post-discharge patient follow-up period using the corresponding clinical deterioration risk detection model. The clinical deterioration risk detection model is a function of health information of the patient in the corresponding post-discharge patient follow-up period and the clinical deterioration risk detection value is configured to predict the likelihood of the clinical deterioration in the patient in the post-discharge patient follow-up period.

In one embodiment, the present patent application includes the above-described four post-discharge patient follow-up periods (e.g., TP, SP, SSP, EOLP), for example, for heart failure patients. In one embodiment, the present patent application includes more than four post-discharge patient follow-up periods. In one embodiment, the present patent application includes less than four post-discharge patient follow-up periods. In one embodiment, the number of the post-discharge patient follow-up periods may vary. In one embodiment, the number of the post-discharge patient follow-up periods may be dependent on the type of chronic health condition of the patient. In one embodiment, the present patent application may include two or more post-discharge patient follow-up periods, for example, for patients with other chronic health conditions. For example, in one embodiment, the present patent application includes two or more post-discharge patient follow-up periods, for example, for chronic obstructive pulmonary disease (COPD) patients. In one embodiment, the present patent application includes two or more post-discharge patient follow-up periods, for example, for kidney failure, liver failure, respiratory failure, or stroke patients. In one embodiment, the present patent application includes two or more post-discharge patient follow-up periods, for example, for patients with co-morbidity. In one embodiment, the present patent application includes two or more post-discharge patient follow-up periods, for example, for patients with multi-morbidity. Various co-morbidities and multi-morbidities include diabetes, kidney problems, or respiratory problems.

Figure 2:
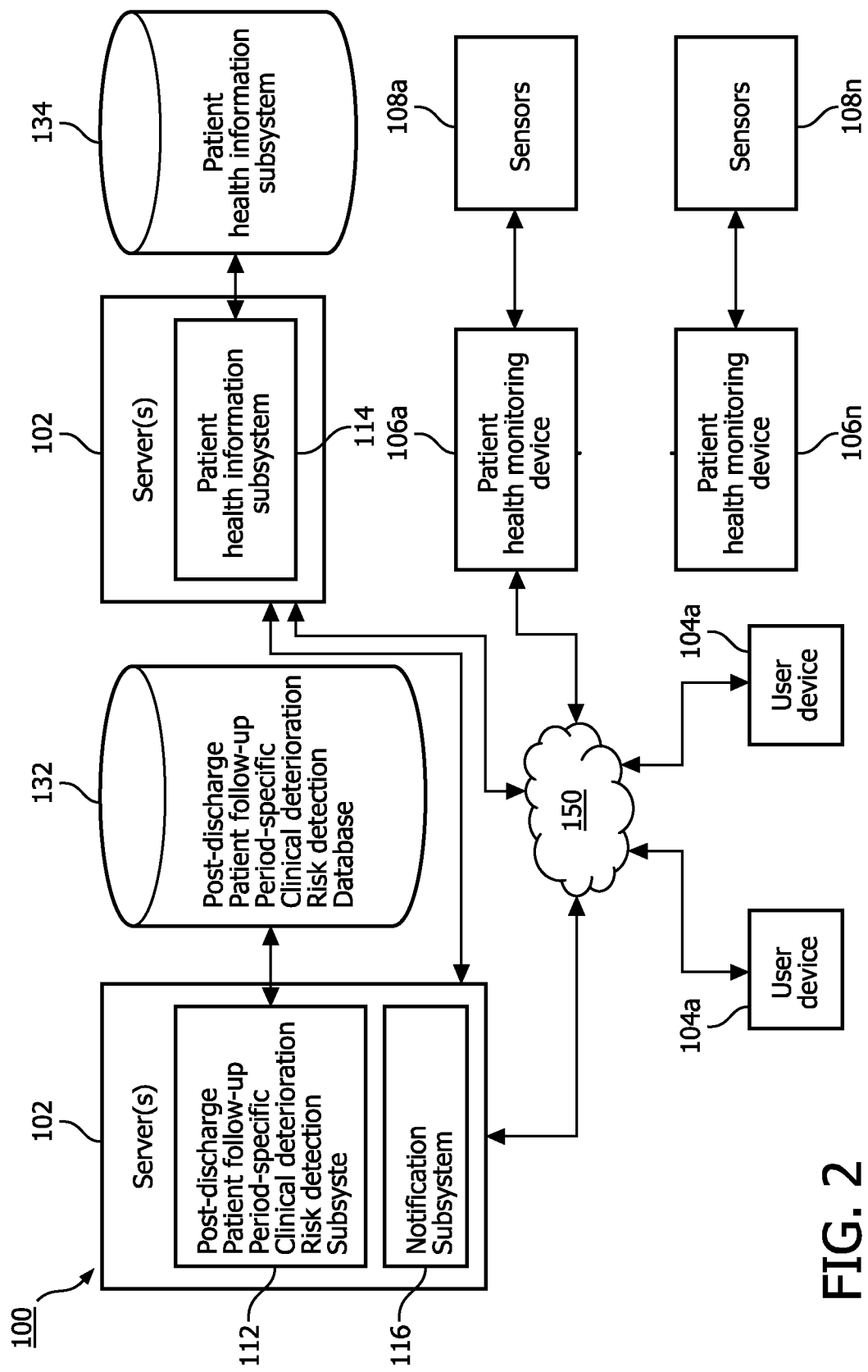
FIG. 2 is an exemplary system for detecting clinical deterioration in patients, on a telehealth service, with a chronic health condition during one or more post-discharge patient follow-up periods in accordance an embodiment of the present patent application.
Figure 3:
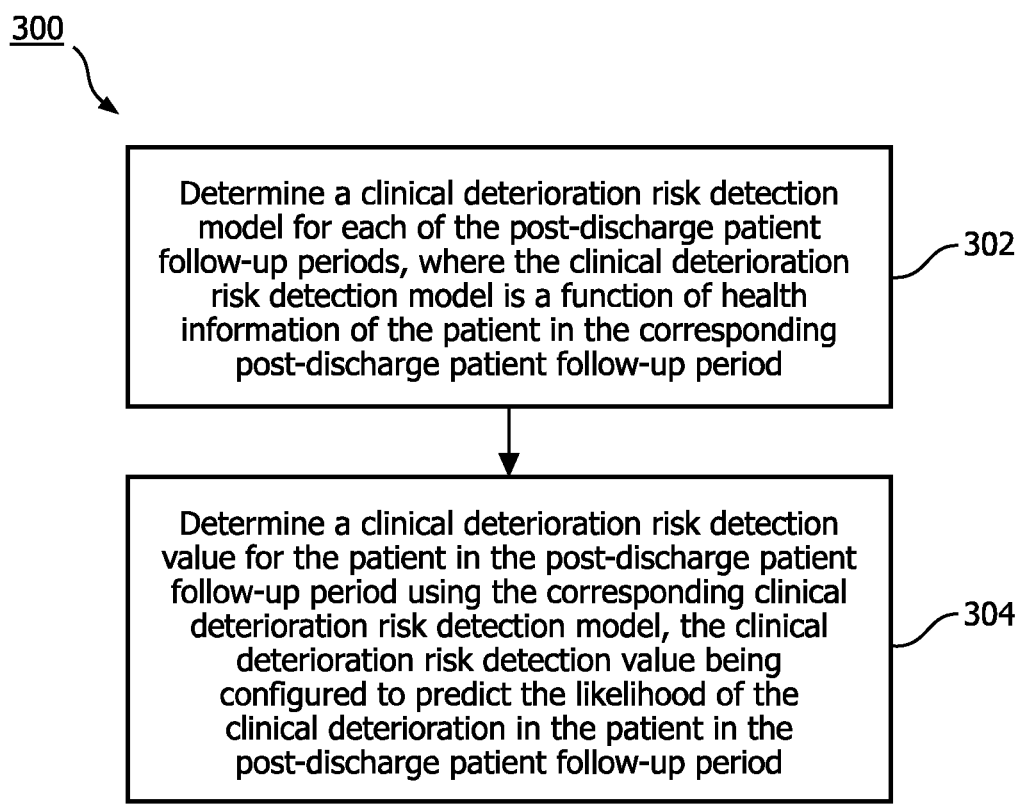
FIG. 3 is a flow chart for detecting clinical deterioration in patients, on a telehealth service, with a chronic health condition during one or more post-discharge patient follow-up periods in accordance an embodiment of the present patent application.
Figure 4:
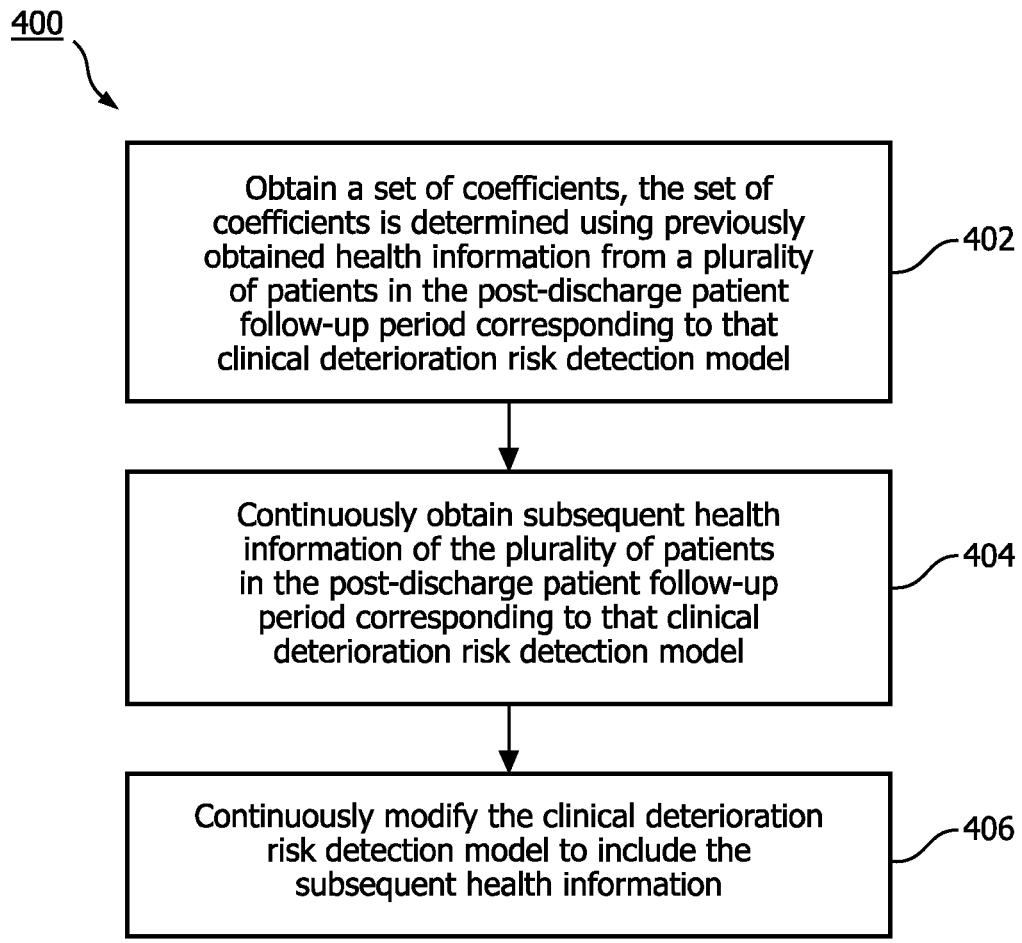
FIG. 4 is a flow chart for updating post-discharge patient follow-up period-specific risk detection models for detecting clinical deterioration in patients, on the telehealth service, with the chronic health condition in accordance an embodiment of the present patent application.

FIG. 2 shows system 100 detecting clinical deterioration in a patient having a health condition during one or more post-discharge patient follow-up periods, in accordance with one or more implementations. As shown in FIG. 2, system 100 may comprise server 102 (or multiple servers 102). Server 102 may comprise post-discharge patient follow-up period-specific clinical deterioration risk detection subsystem 112, patient health information subsystem 114, notification subsystem 116, or other components. In one embodiment, the patient is on a telemedicine, telehealth or telecare service. In one embodiment, the telehealth service is configured to facilitate a medical encounter or an interaction between the patient at a patient site and a provider at a provider site remotely located from the patient.

System 100 may further comprise user device 104 (or multiple user devices 104a-104n). User device 104 may comprise any type of mobile terminal, fixed terminal, or other device. By way of example, user device 104 may comprise a desktop computer, a notebook computer, a tablet computer, a smartphone, a wearable device, or other user device. In some implementations, user device 104 may comprise one or more health monitoring devices and/or sensors thereof (e.g., health monitoring devices 106a-106n, sensors 108a-108n, etc.) for obtaining patient health information. Patients may, for instance, utilize one or more user devices 104 to interact with server 102 or other components of system 100. It should be noted that, while one or more operations are described herein as being performed by components of server 102, those operations may, in some implementations, be performed by components of user device 104 or other components of system 100.

In some implementations, one or more health monitoring devices 106 may be separate and independent from user devices 104 having general functionalities such as those available on common desktop computers, notebook computers, tablet computers, smartphones, etc. Health monitoring devices 106 may comprise weighing scale, temperature monitoring device, heart rate monitoring device, respiration rate monitoring device, blood pressure monitoring device, oxygen saturation monitoring device, glucose monitoring device, or other health monitoring devices.

In one embodiment, system 100 is configured to use a different clinical deterioration risk detection model for each post-discharge patient follow-up time periods when the patients are on the telehealth service. For example, based on the post-discharge patient follow-up time period that the patient is in and using patient health information in the corresponding post-discharge patient follow-up time period, clinical deterioration risk detection value for the patient in that post-discharge patient follow-up time period is determined using the corresponding clinical deterioration risk detection model. The clinical deterioration risk detection value is configured to predict the likelihood of the clinical deterioration in the patient in that post-discharge patient follow-up time period.

In some embodiments, the use of a different clinical deterioration risk detection model for each of the post-discharge patient follow-up periods provides an opportunity to fine-tune the parameters which are highly dependent on the current position on the patient's timeline. Indeed, to prevent an exacerbation in the transitional phase (TP) or in the end-of-life phase (EOLP), different interventions may be used. Each intervention may entail a different time lag between the identification time (e.g., flag raised) and the perceived benefits in the patient. As a consequence, the length of the prediction window (e.g., how many days in advance to predict the adverse event) can be optimized to find an optimal trade-off between the prediction window's length (e.g., influenced by the selected intervention, and the exacerbation velocity in the investigated post-discharge patient follow-up period)) and the predictive power of the clinical deterioration risk detection model.

In some implementations, clinical deterioration risk detection subsystem 112 determines a clinical deterioration risk detection model for each post-discharge patient follow-up period. In some embodiments, clinical deterioration risk detection model generally relates the patient health information (including features (or predictors) on post-discharge information (post-discharge), daily patient vital sign information on body weight (BW), heart rate (HR), oxygen saturation (SpO2), respiration rate (RR) and blood pressure (BP) (including both systolic and diastolic blood pressure) and symptom survey responses on shortness of breath (SoB), fatigue (F), swelling of ankles (SoA)) to the clinical deterioration risk detection value by means of a logistic function and a set of coefficient denoted by β.

In some embodiments, clinical deterioration risk detection subsystem 112 determines clinical deterioration risk detection models for each of the transitional period (TP), the supportive period (SP), the steady state period (SSP), and the end-of-life period (EOLP). Equations (1) through (4) below show clinical deterioration risk detection models for each of the transitional period (TP), the supportive period (SP), the steady state period (SSP), and the end-of-life period (EOLP).

$$CDRV_{TP}=\text{Function}([1\ \text{Patient Health Information}]\ \beta_{TP}) \quad (1)$$

$$CDRV_{SP}=\text{Function}([1\ \text{Patient Health Information}]\ \beta_{SP}) \quad (2)$$

$$CDRV_{SSP}=\text{Function}([1\ \text{Patient Health Information}]\ \beta_{SSP}) \quad (3)$$

$$CDRV_{EOLP}=\text{Function}([1\ \text{Patient Health Information}]\ \beta_{EOLP}) \quad (4)$$

$CDRV_{TP}$, $CDRV_{SP}$, $CDRV_{SSP}$, and $CDRV_{EOLP}$ are the clinical deterioration risk detection values of the transition period (TP), the supportive period (SP), the steady state period (SSP), and the end-of-life period (EOLP), respectively. $\beta_{TP}$, $\beta_{SP}$, $\beta_{SSP}$, and $\beta_{EOLP}$ are the set of coefficients for the transition period (TP), the supportive period (SP), the steady state period (SSP), and the end-of-life period (EOLP), respectively.

In some embodiments, the function in the above equations (1) through (4) is a logistic function or a probability function. In one embodiment, the patient health information in the above equations (1) through (4) includes the coefficient values of the features (or predictors) on post-discharge information (post-discharge), daily patient vital sign readings on body weight (BW), heart rate (HR), respiration rate (RR) and blood pressure (BP) and symptom survey responses on shortness of breath (SoB), fatigue (F), swelling of ankles (SoA).

For example, in equation (1), the patient health information refers to health information of the patient in the transitional period (TP); in equation (2), the patient health information refers to health information of the patient in the supportive period (SP), in equation (3), the patient health information refers to health information of the patient in the steady state period (SP) and in equation (4), the patient health information refers to health information of the patient in the end-of-life period (EOLP).

In some embodiments, features of the patient health information can change in various post-discharge patient follow-up periods dependent on the relevance of those features in that specific post-discharge patient follow-up period. For example, in the transitional period (TP), patient vital sign readings and survey responses of the patient health information are hardly available due to the short follow-up. Post-discharge patient health information, therefore, has a higher weight when determining clinical deterioration risk detection value/score in the transitional period (TP). The post-discharge patient health information generally includes in-hospital treatment information, follow-up coordination information and patient routine information.

In some embodiments, patient vital sign readings and survey responses of the patient health information can have a higher weight when determining clinical deterioration risk detection value/score in the supportive period (SP) and in the steady state period (SSP). In some embodiments, longer time-lag in the features of the patient health information can also be used for the supportive period (SP) and the steady state period (SSP), because of the availability of more patient health information in the supportive period (SP) and the steady state period (SSP).

In some embodiments, clinical deterioration risk detection subsystem 112 is configured to update or modify the clinical deterioration risk detection model for the transitional period (TP) such an increased weight is given to the post-discharge patient health information of the patient health information and a lower weight is given to the patient vital sign readings and the survey responses of the patient health information.

In some embodiments, clinical deterioration risk detection subsystem 112 is configured to update or modify the clinical deterioration risk detection models for the supportive period (SP) and the steady state period (SSP) such an increased weight is given to the patient vital sign readings and the survey responses of the patient health information and a lower weight is given to the post-discharge patient health information of the patient health information.

In some embodiments, clinical deterioration risk detection subsystem 112 is configured to estimate the set of coefficients β from existing or available telehealth patient health information. For example, in some embodiments, the set of coefficients $\beta_{TP}$, used in the clinical deterioration risk detection model for the transitional period (TP), is estimated from the existing telehealth patient health information only from the transitional period (TP). In some embodiments, the set of coefficients $\beta_{SP}$, used in the clinical deterioration risk detection model for the supportive period (SP), is estimated from the existing telehealth patient health information only from the supportive period (SP). In some embodiments, the set of coefficients $\beta_{SSP}$, used in the clinical deterioration risk detection model for the steady state period (SSP), is estimated from the existing telehealth patient health information only from the steady state period (SSP). In some embodiments, the set of coefficients $\beta_{EOLP}$, used in the clinical deterioration risk detection model for the end-of-life period (EOLP), is estimated from the existing telehealth patient health information only from the end-of-life period (EOLP).

In some embodiments, clinical deterioration risk detection subsystem 112 determines the clinical deterioration risk detection model for each of the post-discharge patient follow-up periods by: obtaining a set of coefficients ($\beta_{TP}$, $\beta_{SP}$, $\beta_{SSP}$, $\beta_{EOLP}$, the set of coefficients is determined using previously obtained health information from a plurality of patients in the post-discharge patient follow-up period corresponding to that clinical deterioration risk detection model. In some embodiments, clinical deterioration risk detection subsystem 112 also continuously obtains subsequent health information of the plurality of patients in the post-discharge patient follow-up period corresponding to that clinical deterioration risk detection model. In some embodiments, clinical deterioration risk detection subsystem 112 then continuously modifies or updates the clinical deterioration risk detection model to include the subsequent patient health information.

In some embodiments, the determined clinical deterioration risk detection models may be saved into a database (e.g., post-discharge patient follow-up period-specific clinical deterioration risk detection database 132) and retrieved from the database based on the post-discharge patient follow-up time period the patient is in and/or other criteria. As described above, clinical deterioration risk detection subsystem 112 may continuously update/modify different clinical deterioration risk detection models.

In some implementations, patient health information subsystem 114 may obtain health information associated with a patient in the post-discharge patient follow-up time period of interest. Upon obtainment, the patient health information may be stored (e.g., patient health information database 134, or other storage if not already stored therein).

As another example, the health information may be obtained from one or more health monitoring devices (e.g., weighing scale, temperature monitoring device, heart rate monitoring device, respiration rate monitoring device, blood pressure monitoring device, oxygen saturation monitoring device, or other health monitoring devices). These health monitoring devices may include one or more sensors, such as cameras, microphones, (pulse) oximetry sensors, respiration rate sensors, heart rate sensors, tactile sensors, glucose sensors, accelerometers, gyroscopes, magnetometers, barometric pressure sensors, humidity sensors, temperature sensors (e.g., body temperature sensors, skin temperature sensors, ambient temperature sensors, etc.), skin conductance sensors, global position system (GPS) sensors, proximity sensors, or other sensors. The sensors may, for instance, be configured to obtain health information of the patient (e.g., weight, heart rate, temperature, respiration rate, oxygen saturation and blood pressure, glucose) or other health information related to the patient.

In one scenario, a health monitoring device may obtain patient health information (e.g., based on information from one or more sensors), and provide patient health information to a computer system (e.g., comprising server 102) over a network (e.g., network 150) for processing. In another scenario, upon obtaining the patient health information, the health monitoring device may process the obtained patient health information, and provide processed patient health information to the computer system over a network. In yet another scenario, the health monitoring device may automatically provide patient health information (e.g., obtained or processed) to the computer system (e.g., comprising server 102). If, for instance, the health monitoring device is offline (e.g., not connected to the Internet, not connected to the computer system, etc.), the health monitoring device may store the patient health information and provide the patient health information to the computer system when the health monitoring device comes online (e.g., when the online status is detected by an application of the user device).

As yet another example, the health information of the patient may also be obtained via one or more manual inputs at one or more user devices (e.g., a health monitoring device that is also a user device, a tablet computer, a smartphone, or other user device). In one use case, when a patient is admitted to a hospital for an episode of heart failure or other morbid event, a physician or other hospital staff (e.g., a nurse, technician, etc.) may submit one or more patient observables for the patient during one or more periods of the patient's stay at the hospital (e.g., until the patient is released from the hospital). These patient observables may include predictors submitted on post-discharge information by a physician or other hospital staff (e.g., a nurse, technician, etc.). These patient observables may, for instance, be submitted as health information of the patient to supplement health information obtained via sensors of health monitoring devices or in lieu of the health information that would otherwise be obtained via such sensors. In another use case, after the patient is released from the hospital, the patient or other individual assisting the patient (e.g., the patient's caretaker, the patient's family member, etc.) may submit patient observables for the patient as health information of the patient to supplement health information obtained via sensors of health monitoring devices or in lieu of the measurements that would otherwise be obtained via such sensors. In yet another use case, after the patient is released from the hospital, the patient or other individual assisting the patient (e.g., the patient's caretaker, the patient's family member, etc.) may submit patient reported signs and symptoms as health information of the patient to supplement health information obtained via sensors of health monitoring devices or in lieu of the measurements that would otherwise be obtained via such sensors. The patient observables and patient reported signs and symptoms submitted in the foregoing use cases (e.g., by the physician or other hospital staff, the patient or other individual assisting the patient, etc.) may, for example, be submitted using one or more applications at one or more user devices.

In some cases, the user devices may automatically provide the submitted patient observables to a computer system (comprising server 102). As an example, if a user device is offline (e.g., not connected to the Internet, not connected to the computer system, etc.), one or more applications of the user device may store the information and provide the information to the computer system when the user device comes online (e.g., when the online status is detected by an application of the user device). In this way, for instance, a user need not wait for the user device to come online before submitting patient observables to the user device (or applications thereof), allowing the patient observables to be collected and submitted at any time (e.g., regardless of whether the user device is currently online).

In some implementations, health information subsystem 114 may continuously obtain subsequent health information associated the multiple patients in different post-discharge patient follow-up periods. As an example, the subsequent patient health information may comprise additional patient health information corresponding to a subsequent time (after a time corresponding to patient health information that was used to generate a clinical deterioration risk detection value for the patient). As an example, the subsequent health information may be obtained from one or more health monitoring devices, via one or more manual inputs at one or more user device, or via other approaches. The subsequent health information may be utilized to further update or modify the clinical deterioration risk detection models for each of the post-discharge patient follow-up periods (e.g., new health information may be used to dynamically update or modify the clinical deterioration risk detection models for each of the post-discharge patient follow-up periods), etc.

In some implementations, clinical deterioration risk detection subsystem 112 may determine a clinical deterioration risk detection value for the patient in a particular post-discharge patient follow-up period using the corresponding clinical deterioration risk detection model. The clinical deterioration risk detection value includes a prediction of the likelihood that the patient will sustain or re-sustain a heart failure, a respiratory failure or other morbid event.

In some embodiments, system 100 is configured to determine a single clinical deterioration risk detection score that pertains to the post-discharge patient follow-up period at hand by switching clinical deterioration risk detection models for each post-discharge patient follow-up period boundary. For example, clinical deterioration risk detection subsystem 112 receives health information of the patient in a post-discharge patient follow-up period and receives clinical deterioration risk detection model corresponding to the post-discharge patient follow-up period clinical deterioration risk detection subsystem 112 determines a single clinical deterioration risk detection score using the received health information and received clinical deterioration risk detection model.

In some embodiments, clinical deterioration risk detection subsystem 112 uses a logistic regression model to determine the clinical deterioration risk detection value for a post-discharge patient follow-up period. For example, a logistic regression model is used to score the likelihood of an exacerbation in the short term (e.g., a detection window of one to five or more days) for a heart failure patient on telehealth service. In some embodiments, clinical deterioration risk detection subsystem 112 may also be implemented by other computational learning models or methods. In some embodiments, clinical deterioration risk detection subsystem 112 uses conditional probability functions or models to determine the clinical deterioration risk detection value for a post-discharge patient follow-up period.

In some embodiments, the clinical deterioration risk detection value is a value ranging between 0 and 1. In some embodiments, the clinical deterioration risk detection value is a value ranging between 0 to 100%. In some embodiments, the clinical deterioration risk detection value is a fractional value. In some embodiments, the clinical deterioration risk detection value predicts the likelihood of an exacerbation.

In some implementations, system 100 is configured to use different detection windows for each post-discharge patient follow-up time period when the patients are on the telehealth service. In some implementations, system 100, for each post-discharge patient follow-up period, uses a detection window that is optimized to that post-discharge patient follow-up period. In some implementations, system 100 is configured to use a detection window ranging from one day to a full week dependent on the post-discharge patient follow-up period at hand. That is, in some implementations, for each post-discharge patient follow-up period, clinical deterioration risk detection value predicts the likelihood of an exacerbation in the detection window time period of that post-discharge patient follow-up period.

In some implementations, as the exacerbations in the transitional phase (TP) happen abruptly in time, system 100 uses a shorter detection window for the transitional phase (TP). For example, in some implementations, the shorter detection window may be 1 or 2 days for the transitional phase (TP).

In some implementations, as exacerbations in the supportive phase (SP) phase happen less abruptly and frequently than the transitional phase (TP), system 100 uses a moderate detection window for the supportive phase (SP). For example, in some implementations, the moderate detection window may be 5 days for the supportive phase (SP).

In some implementations, as decompensation builds up over a longer time period during the steady state phase (SSP), system 100 uses a longer detection window for the steady state phase (SSP). For example, in some implementations, the longer detection window may be a week or more for the steady state phase (SSP).

In some implementations, as the patients may need specialized interventions in addition to their telehealth services during the end-of-life phase (EOLP), system 100 uses a sufficiently long detection window for the end-of-life phase (EOLP). For example, in some implementations, the end-of-life phase (EOLP) detection window may be two weeks long or one month long.

In some implementations, the above-described detection windows are, for example, for heart failure patients. In some implementations, the present patent application may include longer or shorter detection windows than described above. In some implementations, the number of days in each detection window may vary. In some implementations, the number days in each detection window may be dependent on the type of chronic health condition of the patient.

In some embodiments, system 100 is configured to determine and present a clinical deterioration risk detection value by weighing the various clinical deterioration risk detection value contributions of each clinical deterioration risk detection model pertaining to the various post-discharge patient follow-up time periods. For example, the weighted clinical deterioration risk detection value is configured to allow for a smooth transition from one post-discharge patient follow-up period to the next post-discharge patient follow-up period. In some embodiments, the weights may change over time.

In some embodiments, clinical deterioration risk detection subsystem 112 determines a clinical deterioration risk detection value by time-adjusted weighing the various clinical deterioration risk detection value contributions of each clinical deterioration risk detection model pertaining to the various post-discharge patient follow-up time periods by using the below equations (5) and (6):

$$CDRV_{Wt[TP\text{-}SP]} = a(t)*CDRV_{TP} + (1-a(t))*CDRV_{SP} \quad (5)$$

$$CDRV_{Wt[SP\text{-}SSP]} = b(t)*CDRV_{SP} + (1-b(t))*CDRV_{SSP} \quad (6)$$

$$CDRV_{Wt[SSP\text{-}EOLP]} = b(t)*CDRV_{SSP} + (1-b(t))*CDRV_{EOLP} \quad (7)$$

In some embodiments, clinical deterioration risk detection subsystem 112 determines a weighted clinical deterioration risk detection value, $CDRV_{Wt[TP\text{-}SP]}$ when a patient is in either the transitional phase (TP) or the supportive phase (SP). For example, the weighted clinical deterioration risk detection value, $CDRV_{Wt[TP-SP]}$ is determined by time-adjusted weighing the clinical deterioration risk detection values of the clinical deterioration risk detection models for the transition period (TP) and the supportive period (SP), for example, by using the equation (5) above. The weight function a(t) is dependent on follow-up time t measured in days and has a range [0, 1]. $CDRV_{TP}$ and $CDRV_{SP}$ are the clinical deterioration risk detection values of the transition period (TP) and the supportive period (SP), respectively.

In some embodiments, clinical deterioration risk detection subsystem 112 determines a weighted clinical deterioration risk detection value, $CDRV_{Wt[SP-SSP]}$ when a patient is in either the supportive phase (SP) or the steady state phase (SSP), etc. For example, the weighted clinical deterioration risk detection value, $CDRV_{Wt[SP-SSP]}$ is determined by time-adjusted weighing the clinical deterioration risk detection values of the clinical deterioration risk detection models for the supportive period (SP) and the steady state period (SSP), for example, by using the equation (6) above. The weight function b(t) is dependent on follow-up time t measured in days and has a range [0, 1]. $CDRV_{SP}$ and $CDRV_{SSP}$ are the clinical deterioration risk detection values of the supportive period (SP) and the steady state period (SSP), respectively.

In some embodiments, clinical deterioration risk detection subsystem 112 determines a weighted clinical deterioration risk detection value, $CDRV_{Wt[SSP-EOLP]}$ when a patient is in either the supportive phase (SSP) or the steady state phase (EOLP), etc. For example, the weighted clinical deterioration risk detection value, $CDRV_{Wt[SSP-EOLP]}$ is determined by time-adjusted weighing the clinical deterioration risk detection values of the clinical deterioration risk detection models for the supportive period (SSP) and the steady state period (EOLP), for example, by using the equation (7) above. The weight function b(t) is dependent on follow-up time t measured in days and has a range [0, 1]. $CDRV_{SSP}$ and $CDRV_{EOLP}$ are the clinical deterioration risk detection values of the supportive period (SSP) and the steady state period (EOLP), respectively.

In some embodiments, system 100 is configured to determine and present all clinical deterioration risk detection values pertaining to the various follow-up time periods as an aggregated clinical deterioration risk detection value. In some embodiments, clinical deterioration risk detection subsystem 112 determines an aggregated clinical deterioration risk detection value by computing the mean of the various clinical deterioration risk detection values of all clinical deterioration risk detection models pertaining to the various post-discharge patient follow-up time periods by using the below equation (8):

$$CDRV_A = \text{mean}(CDRV_{TP}, CDRV_{SP}, CDRV_{SSP}, CDRV_{EOLP}) \quad (8)$$

In some embodiments, clinical deterioration risk detection subsystem 112 determines an aggregated clinical deterioration risk detection value, $CDRV_A$ by computing the mean of the clinical deterioration risk detection value in the transition period, $CDRV_{TP}$, the clinical deterioration risk detection value in the supportive period, $CDRV_{SP}$, the clinical deterioration risk detection value in the steady state period, $CDRV_{SSP}$, and the clinical deterioration risk detection value in the end-of-life period $CDRV_{EOLP}$.

In some implementations, notification subsystem 116 may provide a notification regarding a clinical deterioration risk detection value to one or more other components of system 100. As an example, one or more health monitoring devices having one or more sensors may obtain health information associated with the patient (e.g., measurements of the individual, health conditions of the individual, or other health information) and provide the health information to health information management subsystem 114. After the health information is processed to determine a clinical deterioration risk detection value for the patient in a particular post-discharge patient follow-up period using the corresponding clinical deterioration risk detection model, notification subsystem 116 may provide a notification regarding the clinical deterioration risk detection value to at least one of a physician or other hospital staff (e.g., a nurse, technician, etc.) at the hospital where the patient was admitted for his/her last episode of heart failure or other morbid event; a physician or other staff (e.g., a nurse, technician, etc.) who are currently providing care via the telehealth services to the patient, and the patient's caretaker, the patient's family member, etc. As one example, notification subsystem 116 may provide a notification regarding the clinical deterioration risk detection value via one or more output devices of the health monitoring device via one or more wired or wireless connections. As another example, notification subsystem 116 may provide a notification regarding the clinical deterioration risk detection value to one or more user devices, such as a desktop computer, a notebook computer, a tablet, a smartphone.

A use case scenario for detecting clinical deterioration in a patient having a chronic health condition during one or more post-discharge patient follow-up periods, in accordance with one or more implementations is described below. As an example, in one scenario, a patient may be admitted to a hospital for an episode of heart failure. At the hospital, the patient's observables are entered (by the treating physician or other hospital staff) as patient health information into system 100 at a time point close to release from the hospital.

When the patient goes home, the treating medical specialist may tell the patient that he has to continue taking his drugs and would like to have him to provide his health information such as his weight, temperature, heart rate, respiratory rate, oxygen saturation, and blood pressure, report his health related signs and symptoms including edema, fatigue, activity, shortness of breath, and swelling of ankles, and fill in a questionnaire with sign and symptoms (e.g., normal daily activities the patient has trouble performing because of fatigue, shortness of breath when the patient is walking one flight of stairs, etc.). This patient health information is provided as input to system 100, and the output of system 100 (e.g., a clinical deterioration risk detection value) may be provided to the patient, the patient's general practitioner, the patient's medical specialist, or other individual. As an example, after some time, system 100 may flag an alert as a result of the determined clinical deterioration risk detection value. Based on this alert, the patient's physician (e.g., general practitioner, medical specialist, etc.) may recommend an early and immediate intervention for the patient. In some embodiment, clinical deterioration risk detection values are visually provided on a telehealth clinical dashboard or display.

In some embodiments, system 100 is described by taking the care provided to a heart failure patient as an example. It would be appreciated by one skilled in the art that system 100 is equally applicable for telehealth-mediated care delivery for patients with other long-term conditions such as COPD.

In some embodiments, the clinical deterioration may include acute worsening of clinical status/symptoms. For example, for the heart failure patients, the clinical deterioration may include cardiopulmonary arrest. In one embodiment, for the COPD patients, the clinical deterioration may include acute respiratory. For example, for the chronically ill patients, the clinical deterioration may include an admission to an emergency care.

In some embodiments, system 100 may be useful in clinical deterioration detection in the telehealth service in which a professional needs to decide on an early and immediate intervention for a monitored patient on the basis of an estimated short-term risk on the patient's exacerbation. In some embodiments, system 100 may also be useful in personal emergence response systems in which a call center agent/personnel needs to decide on an intervention for a subscriber or patient on the basis of a short-term estimated risk for a hospital transport. In some embodiments, system 100 may be used in hospital to home programs; clinical programs in ambulatory care, and/or readmission prevention programs. In some embodiments, system 100 may also be used in home monitoring programs; personal emergency response systems, etc.

In some implementations, the various computers and subsystems illustrated in FIG. 2 may comprise one or more computing devices that are programmed to perform the functions described herein. The computing devices may include one or more electronic storages (e.g., post-discharge patient follow-up period-specific clinical deterioration risk detection database 132, patient health information database 134, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, a digital circuit designed to process information, an analog circuit designed to process information, a state machine, and/or other mechanisms for electronically processing information. In some implementations, the processors may include a plurality of processing units. These processing units may be physically located within the same device, or the processors may represent processing functionality of a plurality of devices operating in coordination. The processors may be programmed to execute computer program instructions to perform functions described herein of subsystems 112-116 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-116 described herein is for illustrative purposes, and is not intended to be limiting, as any of subsystems 112-116 may provide more or less functionality than is described. For example, one or more of subsystems 112-116 may be eliminated, and some or all of its functionality may be provided by other ones of subsystems 112-116. As another example, additional subsystems may be programmed to perform some or all of the functionality attributed herein to one of subsystems 112-116.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A computer system configured to detect clinical deterioration in a patient having a health condition during a plurality of post-discharge patient follow-up periods, comprising:

one or more computer processors;

one or more computer readable storage devices;

program instructions to determine one or more different clinical deterioration risk detection models for each of the plurality of post-discharge patient follow-up periods, wherein each of the one or more different clinical deterioration risk detection models corresponds to a different function of health information of the patient in the corresponding post-discharge patient follow-up period, and wherein each the one or more clinical deterioration risk detection model is selected from one or more of a transitional period, a supportive period, a steady state period, and an end of life period;

program instructions to determine a clinical deterioration risk detection value for the patient in the corresponding post-discharge patient follow-up period using a corresponding clinical deterioration risk detection model, the clinical deterioration risk detection value being configured to predict the likelihood of the clinical deterioration in the patient in the corresponding post-discharge patient follow-up period;

program instructions to flag an alert as a result of the determined clinical deterioration risk detection value for the corresponding post-discharge patient follow-up period; and based upon the alert, program instructions to direct an intervention for the patient, wherein different interventions are used and each intervention has a different time lag related to the corresponding post-discharge patient follow-up period.

2. The computer system of claim 1, further comprising:

one or more remote health monitoring devices, each of which comprises one or more sensors programmed to obtain health information of the patient;

program instructions to obtain, based on the sensors, the health information of the patient in the corresponding post-discharge patient follow-up period; and program instructions to provide the health information of the patient in the corresponding post-discharge patient follow-up period to the computer system, wherein the computer system determines the clinical deterioration risk detection value for the patient in the post-discharge patient follow-up period by obtaining the health information of the patient in the corresponding post-discharge patient follow-up period and using the corresponding clinical deterioration risk detection model.

3. The computer system of claim 1, wherein the computer system determines the clinical deterioration risk detection model for each of the post-discharge patient follow-up periods by:

obtaining a set of coefficients, the set of coefficients being determined using previously obtained health information from a plurality of patients in the post-discharge patient follow-up period corresponding to that clinical deterioration risk detection model;

continuously obtaining subsequent health information of the plurality of patients in the post-discharge patient follow-up period corresponding to that clinical deterioration risk detection model; and continuously modifying the clinical deterioration risk detection model to include the subsequent health information.

4. The computer system of claim 1, wherein the computer system determines a weighted clinical deterioration risk detection value for the patient using the clinical deterioration risk detection values for the patient in two or more of the post-discharge patient follow-up periods.

5. The computer system of claim 1, wherein the computer system determines an aggregated clinical deterioration risk detection value for the patient using the clinical deterioration risk detection values for the patient in each of the post-discharge patient follow-up periods.

6. A method for detecting clinical deterioration in a patient having a health condition during a plurality of post-discharge patient follow-up periods, the method being implemented by a computer system that comprises one or more physical processors executing computer program instructions which, when executed, perform the method comprising:

determining, by the computer system, one or more different clinical deterioration risk detection models for each of the plurality of post-discharge patient follow-up periods, wherein each of the one or more different clinical deterioration risk detection models corresponds to a different function of health information of the patient in the corresponding post-discharge patient follow-up period, and wherein each of the one or more clinical deterioration risk detection model is selected from one or more of a transitional period, a supportive period, a steady state period, and an end of life period;

determining, by the computer system, a clinical deterioration risk detection value for the patient in the corresponding post-discharge patient follow-up period using a corresponding clinical deterioration risk detection model, the clinical deterioration risk detection value being configured to predict the likelihood of the clinical deterioration in the patient in the corresponding post-discharge patient follow-up period;

flagging an alert as a result of the determined clinical deterioration risk detection value for the corresponding post-discharge patient follow-up period; and based upon the alert, directing an intervention for the patient, wherein different interventions are used and each intervention has a different time lag related to the corresponding post-discharge patient follow-up period.

7. The method of claim 6, further comprising:

obtaining, by the computer system, from one or more remote health monitoring device comprising one or more sensors, the health information of the patient in the corresponding post-discharge patient follow-up period; and determining, by the computer system, the clinical deterioration risk detection value for the patient in the post-discharge patient follow-up period by using the obtained health information of the patient in the corresponding post-discharge patient follow-up period and using the corresponding clinical deterioration risk detection model.

8. The method of claim 6, further comprising:

obtaining, by the computer system, a set of coefficients, the set of coefficients being determined using previously obtained health information from a plurality of patients in the post-discharge patient follow-up period corresponding to that clinical deterioration risk detection model;

continuously obtaining, by the computer system, subsequent health information of the plurality of patients in the post-discharge patient follow-up period corresponding to that clinical deterioration risk detection model; and continuously modifying, by the computer system, the clinical deterioration risk detection model to include the subsequent health information.

9. The method of claim 6, further comprising:

determining, using the computer system, a weighted clinical deterioration risk detection value for the patient using the clinical deterioration risk detection values for the patient in two or more of the post-discharge patient follow-up periods.

10. The method of claim 6, further comprising:

determining, using the computer system, an aggregated clinical deterioration risk detection value for the patient using the clinical deterioration risk detection values for the patient in each of the post-discharge patient follow-up periods.

11. A non-transitory medium comprising machine-readable instructions executed by at least one process to detect clinical deterioration in a patient having a health condition during a plurality of post-discharge patient follow-up periods, the non-transitory medium system comprising:
- instructions for determining one or more different clinical deterioration risk detection models for each of plurality of the post-discharge patient follow-up periods, wherein each of the one or more different clinical deterioration risk detection model corresponds to a different function of health information of the patient in the corresponding post-discharge patient follow-up period, and wherein each the one or more clinical deterioration risk detection model is selected from one or more of a transitional period, a supportive period, a steady state period, and an end of life period;
- instructions for determining a clinical deterioration risk detection value for the patient in the corresponding post-discharge patient follow-up period using a corresponding clinical deterioration risk detection model, the clinical deterioration risk detection value being configured to predict the likelihood of the clinical deterioration in the patient in the corresponding post-discharge patient follow-up period;
- instructions for flagging an alert as a result of the determined clinical deterioration risk detection value for the corresponding post-discharge patient follow-up period; and
- based upon the alert, instructions for directing an intervention for the patient, wherein different interventions are used and each intervention has a different time lag related to the corresponding post-discharge patient follow-up period.

12. The non-transitory medium of claim 11, further comprising:
- instructions for obtaining from one or more remote health monitoring device comprising one or more sensors, the health information of the patient in the corresponding post-discharge patient follow-up period; and
- instructions for determining the clinical deterioration risk detection value for the patient in the post-discharge patient follow-up period by using the obtained health information of the patient in the corresponding post-discharge patient follow-up period and using the corresponding clinical deterioration risk detection model.

13. The non-transitory medium of claim 11, further comprising:
- instructions for obtaining a set of coefficients, the set of coefficients being determined using previously obtained health information from a plurality of patients in the post-discharge patient follow-up period corresponding to that clinical deterioration risk detection model;
- instructions for continuously obtaining subsequent health information of the plurality of patients in the post-discharge patient follow-up period corresponding to that clinical deterioration risk detection model; and
- instructions for continuously modifying the clinical deterioration risk detection model to include the subsequent health information.

14. The non-transitory medium of claim 11, further comprising
- instructions for determining a weighted clinical deterioration risk detection value for the patient using the clinical deterioration risk detection values for the patient in two or more of the post-discharge patient follow-up periods.

15. The non-transitory medium of claim 11, further comprising
- instructions for determining an aggregated clinical deterioration risk detection value for the patient using the clinical deterioration risk detection values for the patient in each of the post-discharge patient follow-up periods.

* * * * *